United States Patent
Stein

[11] Patent Number: 5,878,912
[45] Date of Patent: Mar. 9, 1999

[54] DUCT DISINFECTING METHOD AND APPARATUS

[76] Inventor: Myron Stein, 1776 Peachtree St., NW. Suite 350-B, Atlanta, Ga. 30309

[21] Appl. No.: 579,632

[22] Filed: Dec. 26, 1995

[51] Int. Cl.⁶ .................................................... G01F 11/00
[52] U.S. Cl. ........................... 222/1; 222/47; 222/154; 222/402.1; 222/529; 239/567
[58] Field of Search .................. 222/1, 47, 154, 222/155, 402.1, 527, 529, 566, 635; 239/337, 559, 567

[56] References Cited

U.S. PATENT DOCUMENTS

| | | | |
|---|---|---|---|
| 2,968,441 | 1/1961 | Holcomb | 239/337 |
| 3,064,863 | 11/1962 | Mattson | 222/155 X |
| 3,186,645 | 6/1965 | Eberlein | 239/567 |
| 3,224,645 | 12/1965 | Frost | 222/182 |
| 3,305,144 | 2/1967 | Beres et al. | 222/402.1 |
| 3,428,224 | 2/1969 | Eberhardt et al. | 222/402.1 |
| 4,024,989 | 5/1977 | Wessel | 222/154 |
| 4,096,974 | 6/1978 | Haber et al. | 222/402.1 |
| 4,682,713 | 7/1987 | Clapp | 222/513 |
| 4,802,535 | 2/1989 | Bakke | 239/567 |
| 4,979,638 | 12/1990 | Bolduc | 222/1 |
| 5,071,035 | 12/1991 | Kiplinger | 222/83.5 |
| 5,154,323 | 10/1992 | Query et al. | 222/513 |
| 5,294,021 | 3/1994 | Docker, III et al. | 239/567 X |
| 5,307,964 | 5/1994 | Toth | 222/402.1 |

*Primary Examiner*—Joseph A. Kaufman
*Attorney, Agent, or Firm*—Womble Carlyle Sandridge & Rice, PLLC

[57] ABSTRACT

An apparatus for disinfecting the interior surfaces of air conditioning ducts comprises a pressurized aerosol canister having a nozzle and an elongated flexible tubular extension coupled to the nozzle. The extension is closed on its free end and is provided along a portion of its length with an array of outlet ports or holes. When the nozzle is actuated, liquid disinfectant is delivered through the array of holes in the form of an aerosol spray or mist that issues in all directions from the tubular extension. In use, the end of the tubular extension is inserted into an air conditioning duct up to a visual indicator provided on the tube. The nozzle is then depressed, which causes an aerosol cloud to be expelled on the inside of the duct coating the interior surfaces of the duct and disinfecting against mold, mildew, and bacteria.

10 Claims, 2 Drawing Sheets

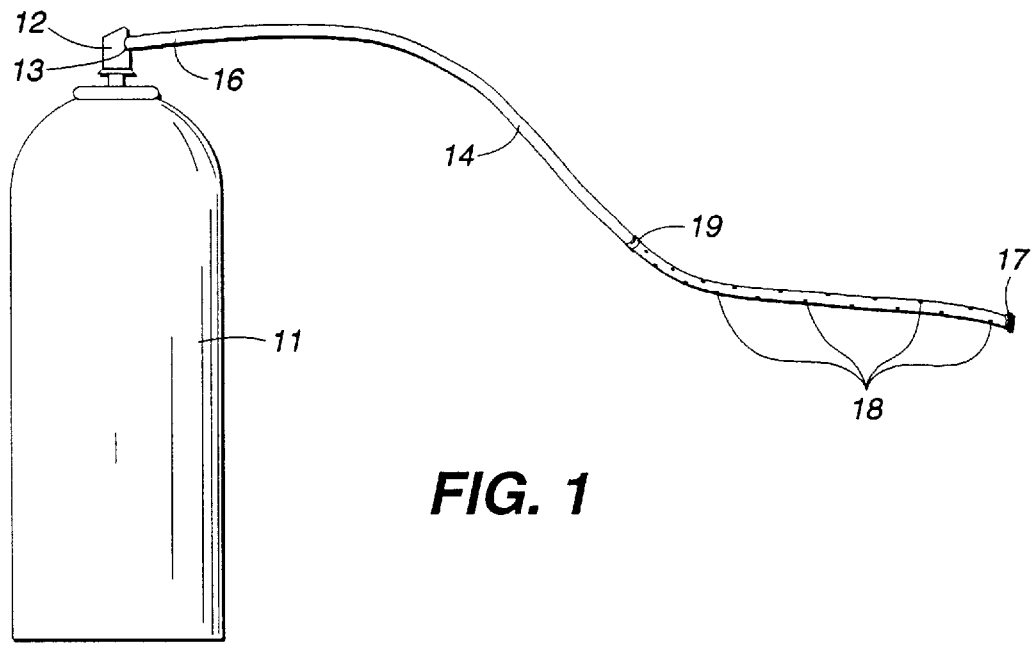
FIG. 1
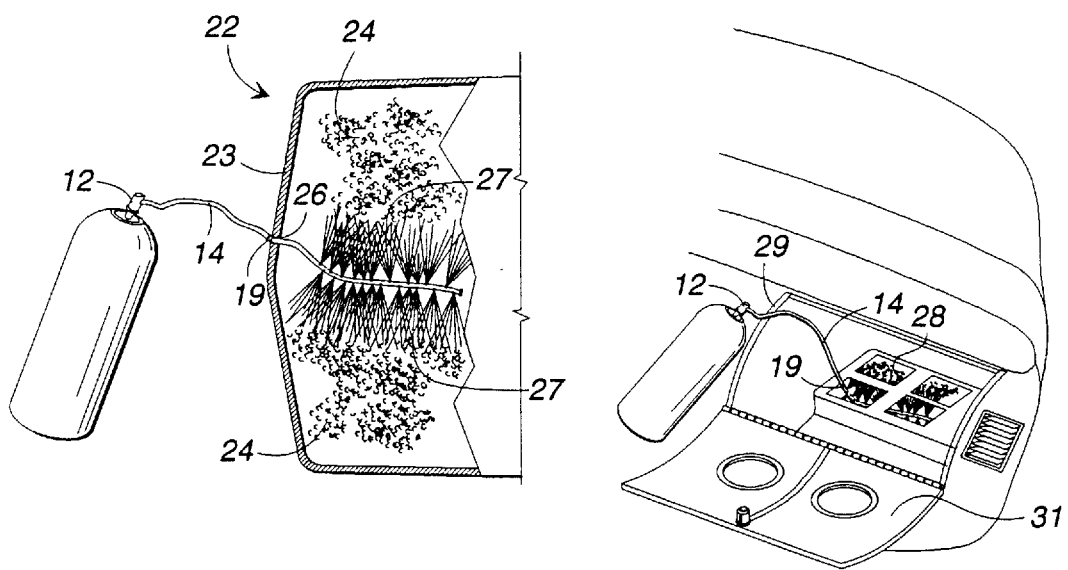
FIG. 3A  FIG. 3B

DUCT DISINFECTING METHOD AND APPARATUS

TECHNICAL FIELD

The present invention relates generally to methods and devices for delivering liquids to a closed area and more particularly to a method and apparatus for delivering an aerosol cloud of disinfectant to the interior of air conditioning and other ducts.

BACKGROUND OF THE INVENTION

A common problem with duct work used for ventilation is the accumulation of mold, mildew, and bacteria on the interior surfaces of the duct work. This problem is particularly acute in automotive air conditioning systems because, unlike home air conditioning systems, automotive air conditioning systems are subject to the warm moist conditions of the outdoors. As a result, the interior walls of automotive air conditioning ducts commonly become a breeding ground for mold, mildew, and bacteria and can even support certain viruses that are harmful to human health. This problem usually manifests itself in the form of stale dank-smelling air issuing from the registers of the air conditioning system. In addition, the mold and mildew that can accumulate in the ducts can irritate the lungs and sinuses of passengers and can even bring on allergic reactions among those susceptible to such contaminants.

In the past, it has been difficult and expensive to remove built-up mold, mildew, and bacteria from the interior duct work of automobile air conditioning systems. This is because the duct work tends to be small, convolutely-shaped, substantially closed, and usually located between the dash and firewall of the vehicle. In extreme cases, it has been necessary to remove the dashboard and the duct work, disassemble the duct work, clean it with appropriate disinfectants, reassemble it, and reinstall the duct work and dashboard. Clearly, this is a time-consuming and very expensive procedure.

It has been possible simply to spray aerosol disinfectants into the intake vents or recirculation vents of automotive air conditioning systems in an attempt to disinfect the interiors of the duct work. While this approach can be somewhat successful, it nevertheless is plagued with numerous problems and shortcomings. In particular, the aerosol that is sprayed into the intake vents generally does not deposit itself on the interior walls of the duct work. This is because the aerosol simply follows the air stream through the system and is ejected from the registers into the car. In the process, most of the interior surface area of the ducts and particularly convolutely-shaped portions thereof remain untouched by the disinfectant.

The use of flexible tubular extensions for aerosol dispensers can improve the effectiveness of common aerosol disinfectants by inserting the tube into the intake vents of the vehicle. However, the liquid disinfectant that issues from the free end of the tube is very directional. Since the interior of the duct work remains unseen by the user, it is virtually impossible to ensure thorough coverage of the disinfectant on the interior surfaces of the duct work. As a result, this type of blind application of disinfectant through a tubular extension has not proven successful in eliminating built-up contaminants.

Thus, there exists a need for a method and apparatus that assures effective and thorough distribution of a disinfectant on the interior surfaces of air conditioning ducts to kill accumulated mold, mildew, and bacteria. The method and apparatus should be reliable, inexpensive, quick, effective, and should require no or minimal disassembly of the automotive air conditioning system. Such a method and apparatus should provide all of these benefits, even in a situation where one cannot see the interior of the air conditioning duct work being treated. It is to the provision of such a method and apparatus that the present invention is primarily directed.

SUMMARY OF THE INVENTION

Briefly described, the present invention, in a preferred embodiment thereof, comprises an apparatus for delivering a liquid aerosol disinfectant to the interior duct work of an automotive air conditioning system to treat the air conditioning system for accumulated mold, mildew, and bacteria. The apparatus comprises a dispenser containing liquid disinfectant to be delivered to the air conditioning duct work. A selectively actuatable nozzle is coupled to the dispenser for expelling liquid from the dispenser and propellant means, such as compressed air, is provided in the dispenser for forcing the liquid disinfectant therein from the dispenser to the nozzle under pressure. An elongated flexible tube having a interior passageway, and open end, and a closed end, is coupled at its open end to the nozzle for receiving liquid under pressure therefrom.

A plurality of small holes or outlet ports are formed along the length of the flexible tube from its closed end to a position intermediate its ends. The holes are arrayed about the circumference of the tube. With this configuration, liquid disinfectant expelled through the nozzle travels through the tube and is issued through the plurality of small holes as a fine aerosol mist or cloud that sprays outwardly in all directions around the tube. A visual indicator is provided on the tube at a position beyond the extent of the array of small holes. The visual indicator provides a gauge for determining when the tube has been inserted the proper amount into a duct to be treated.

In using the apparatus of this invention to perform the method of the invention, the perforated flexible tube is inserted into the interior portion of an air conditioning duct to be treated. For this purpose, the tube can be inserted through an existing vent, such as the recirculation vent under the glove box or, alternatively, a small hole can be drilled in the wall of a duct and the tube can be inserted through the hole. The tube is inserted into the duct up to the position of the visual indicator. This ensures that the end of the tube bearing the array of small holes is properly positioned within the duct. The nozzle is then activated, which causes an aerosol cloud to issue from the array of holes within the duct. This cloud sprays out in all directions from the tube so that the entire interior surface of the duct becomes covered with the disinfectant. After an appropriate time, the disinfectant acts to kill the mold, mildew, and bacteria within the duct work, thus eliminating the musty smell within the automobile and reducing greatly sources of allergic reaction.

Thus, it is an object of this invention to prove a simple and efficient method of disinfecting the interior surfaces of automotive air conditioning duct work.

It is another object of the invention to provide an apparatus for delivering a liquid aerosol disinfectant to the interior duct work of an automotive air conditioning system that is inexpensive, simple to manufacture, yet effective and repeatable.

A still further object of the invention is to provide a method of disinfecting the interior duct work of automobile air conditioning systems that does not require any disassembly of the automobile or of its air conditioning duct work.

An additional object of the invention is to provide a method and apparatus for disinfecting the interior duct work of automotive air conditioning systems that is as effective as disassembling the system and cleaning it but that requires much less time, expense, and effort.

These and other objects, features, and advantages will become more apparent upon review of the detailed description set forth below taken in conjunction with the accompanying drawings, which are briefly described as follows.

BRIEF DESCRIPTION OF THE DRAWINGS

FIG. 1 is a side elevational view of an apparatus that embodies principles of the present invention in a preferred form.

FIG. 3A illustrates one way of performing the method of this invention.

FIG. 3B illustrates an alternate way of performing the method of the invention.

DETAILED DESCRIPTION OF THE PREFERRED EMBODIMENT

Figure 2:
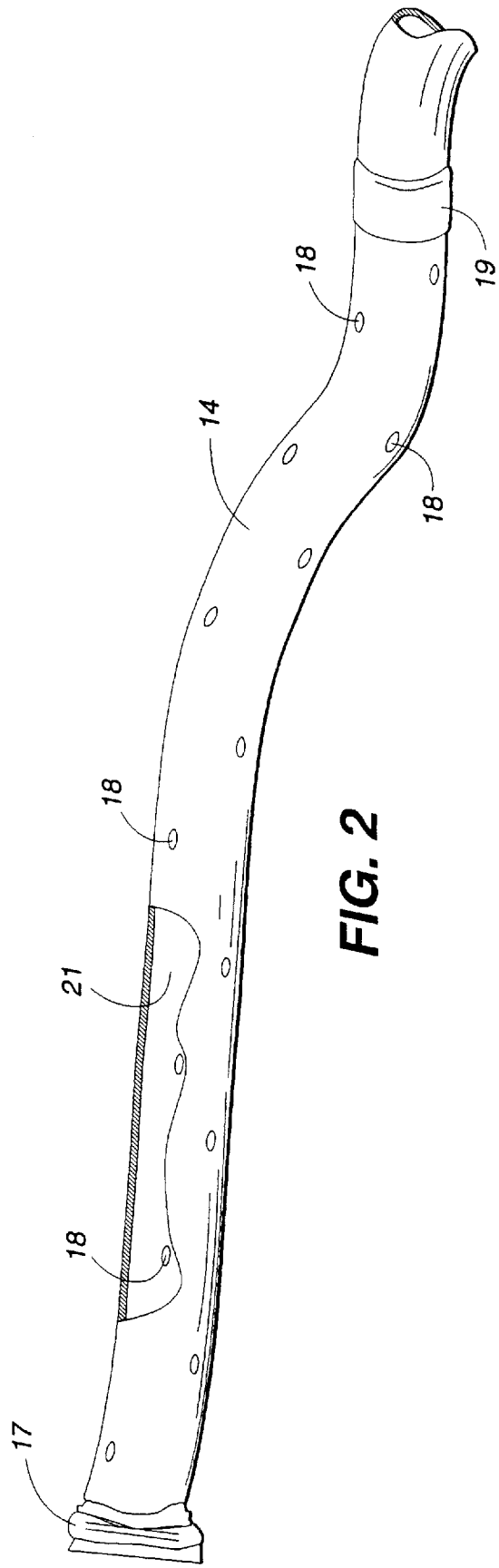
FIG. 2 is a magnified partially sectioned view of the flexible tube of this invention showing the plurality of outlet ports arrayed along the length of the tube.

Referring now to the drawings in which like numerals refer to like parts throughout the several views, FIG. 1 illustrates an apparatus that embodies principles of the present invention in a preferred form. The apparatus comprises a dispenser 11 for containing liquid disinfectant to be delivered to the interior of an automotive air conditioning system. In the preferred embodiment, the dispenser 11 comprises a pressurized aerosol container containing the disinfectant liquid and a propellant. While this is considered to be preferred, it nevertheless should be understood that other means of dispensing the disinfectant liquid could also be employed. For example, a reservoir of liquid and a separate pressurized propellant could be used, particularly in large volume commercial operations. However, it has been found that the pressurized aerosol canister provides an apparatus that is easy to use and effective.

A selectively actuatable nozzle 12 is coupled to the dispenser 11 and is adapted, upon being actuated with the pressure of a finger, to receive and expel liquid disinfectant from the dispenser 11. The nozzle 12 functions in the usual way, expelling liquid from the dispenser 11 through a nozzle outlet 13.

An elongated flexible tube 14 has a first end 16 and a second end 17. The first end 16 is open and is coupled to and communicates with the nozzle outlet 13 of the nozzle 12. Liquid expelled from the nozzle is delivered directly to the interior passageway of the tube 14. In the preferred embodiment, the second end of the tube 17 is closed off. The preferred method of closing off the second end 17 is simply to heat seal the end together with a heated sealing element. Nevertheless, equivalent methods of sealing off the end 17 might also be used, such as inserting a plug in the end or folding the end over on itself. Furthermore, while it is preferred that the end 17 be closed off, it could, if desired, be left open such that sealing the end 17 should not be considered a limitation of the present invention but only an exemplary embodiment.

A plurality of small holes or outlet ports 18 are formed in the tube 14 and communicate with the interior passageway thereof. The holes 18 are arrayed along the length of the tube 14 from its second end 17 to a position intermediate its first and second ends 16 and 17 respectively. The pattern of the array of holes 18 can affect the effectiveness of the method of this invention. This pattern will be discussed in more detail below; however, in general, the holes 18 are arrayed around the perimeter of the tube 14. With such a configuration when the nozzle 12 is actuated, liquid disinfectant from the dispenser 11 is delivered through the tube 14 and is expelled through the array of holes 18 in the form of a fine mist or aerosol cloud that issues in all directions around the tube. As detailed below, this method of expelling the liquid ensures that the interior surfaces of air conditioning ducts are thoroughly covered and treated with the liquid disinfectant from the dispenser 11.

A visual indicator in the form of a ringed mark 19 is provided on the tube 14 at a position beyond the extent of the array of holes 18. The location of the indicator 19 is preselected to ensure that when the tube is inserted into an air conditioning duct up to the indicator 19, the end portion of the tube containing the array of holes 18 is properly positioned within the duct for delivering the liquid disinfectant most efficiently thereto.

FIG. 2 is a closeup partially sectioned view of the free end and intermediate portion of the tube 14 showing details thereof. The tube 14 is seen to have an interior passageway 21 that extends along the length of the tube. The second end 17 of the tube has been sealed shut by means of a heated sealing element so that liquid moving down the passageway 21 is restricted to escape through the outlet ports or holes 18 formed along the length of the tube. This has been found to provide for an aerosol cloud or mist that migrates through and covers the interior surfaces of the duct work.

The holes 18 are arrayed along the length of the tube 14 from a position adjacent to its second end 17 to a position intermediate its ends 16 and 17. In the preferred embodiment, the holes 18 are arrayed in two lines; one along one side of the tube 14 and one along the other side of the tube 180 degrees from the first line. In addition, the holes along one line are longitudinally shifted one-half the distance between respective holes so that the holes on one side of the tube are staggered with respect to the holes on the other side of the tube. It has been found that a spacing between adjacent holes of approximately 0.75 inches provides superior results for treating the interior surfaces of automotive air conditioning duct work. In addition, a total length from the second end 17 to the visual indicator 19 of approximately 4.25 inches has been found to position the perforated end portion of the tube appropriately within air conditioning duct systems. It should be clearly understood, however, that these dimensions, while having been found to function well for their intended purpose, are not limiting and that various other distances might be employed with comparable results for a given purpose. In addition, the opposed staggered array of holes 18 should be understood to be only an exemplary embodiment. The holes could just as well be arrayed at 90 degree increments or anywhere in between and could be staggered or positioned with respect to each other in any of a myriad of different configurations. All of these variations as well as combinations thereof might well be selected and employed by those of skill in the art within the scope of the present invention.

FIG. 3A illustrates one way in which the method of the present invention can be performed. In this embodiment, an automotive air conditioning duct 22 has a wall 23 and interior surfaces 24. In this embodiment of the method, a small hole 26 is drilled in the wall 23 of the duct 22. The tube 14, coupled to the nozzle 12, is then inserted through the hole 26 up to the position of the visual indicator 19. The nozzle 12 is then depressed, which delivers liquid disinfectant from the dispenser 11 into and through the tube 14. As the liquid disinfectant moves through the tube, it is ejected in the form of an aerosol spray or mist 27 within the duct 22. Because of the positioning of the holes 18 around the perimeter of the tube 14, the aerosol cloud issues from the tube in all directions within the duct. As a result, the aerosol disinfectant from the dispenser 11 is deposited evenly and thoroughly over the inner surfaces 24 of the duct. Thus, mold, mildew, and bacteria are destroyed over virtually the entire surface area of the duct interior. When the duct 22 has been completely treated and disinfected through this method, the tube 14 is removed from the hole 26, and the hole can be plugged with a small rubber plug or with putty leaving behind a cleaned and disinfected air conditioning duct.

FIG. 3B illustrates an alternate way of performing the method of this invention. In this embodiment, the aerosol disinfectant is delivered to the recirculation vent 28 of the air conditioning system, which usually is located behind the glove box 29. In this embodiment of the method, the door 31 of the glove box 29 is opened and the interior lining of the glove box removed to reveal the recirculation vent 28. The tube 14 of the present invention is inserted into the recirculation vent 28 up to the visual indicator 19. The nozzle 12 is then depressed to deliver the aerosol disinfectant to the interior of the duct work in the form of an aerosol spray or cloud that covers and disinfects the interior of the duct. While this embodiment of the method requires some disassembly of the dash elements, it does not require that small holes be drilled in the duct work and then filled. In addition, this embodiment of the method has been found somewhat effective when the air conditioning fan is running to help deposit the disinfecting liquid on the interior surfaces of the ducts.

In addition to the foregoing two embodiments of the present method, it will be understood that there may well be various and other embodiments of performing the method including, but not limited to, inserting the tube 14 through the exterior intake vents of the system, inserting the tube into the outlet registers of the system, or inserting the tube into any other orifice that would position the perforated end of the tube within a duct of the air conditioning system. In addition, a variety of schemes for applying the disinfectant utilizing the fan, heating system, and cooling system of the vehicle might be employed to assure effective thorough treatment. Finally, it will be clear that the method and apparatus of this invention has application in a variety of situations other than vehicle vent systems where a liquid aerosol is to be delivered to the interior surfaces of a closed space. Accordingly, it will be clear that the embodiments illustrated in FIGS. 3A and 3B are exemplary only and not intended to be limiting aspects of the present invention.

The invention has been described herein in terms of preferred embodiments and methodologies. It will be clear to those of skill in this art, however, that various modifications, additions, and deletions might be made to the illustrated embodiments without departing from the spirit and scope of the invention as set forth in the claims.

I claim:

1. A method of disinfecting the interior surfaces of the duct work of an automotive air conditioning system, said method comprising the steps of:

(a) providing an elongated flexible tube constructed from a heat sealable material having a first end, a second closed end, and a plurality of outlet ports formed at least partially along the length of said tube, said outlet ports being constructed and arranged to form at least a first row of outlet ports and a second row of outlet ports, the first row of outlet ports being longitudinally and circumferentially offset from the second row of outlet ports along said tube;

(b) coupling the elongated tube at its first end to a source of disinfectant under pressure;

(c) inserting the elongated flexible tube into the interior duct work of an automotive air conditioning system to a depth sufficient to locate the plurality of outlet ports inside the duct work; and (d) expelling liquid disinfectant from the source through the elongated tube to eject disinfectant from the plurality of outlet ports as an aerosol cloud within the duct work for thoroughly treating the interior surfaces of the duct work.

2. The method of claim 1 wherein step (a) includes the step of heat sealing the second end of said elongated flexible tube.

3. The method of claim 1 and further comprising the step of providing a visual indicator on the elongated tube for gauging the depth to which the tube is to be inserted into the duct work and wherein step (c) includes inserting the elongated tube into the interior duct work to the depth indicated by the visual indicator to optimally position the plurality of outlet ports within the duct work to facilitate complete treatment of the interior surfaces of the duct work.

4. The method of claim 3 and where in step (a) the second end of the elongated tube is heat sealed.

5. The method of claim 4 and where in step (b) the source of disinfectant under pressure is an aerosol dispenser.

6. The method of claim 3 further comprising the step of positioning the plurality of outlet ports between the second closed end of said elongated flexible tube and said visual indicator.

7. The method of claim 1 wherein step (a) includes the step of offsetting the first row of outlet ports 180° from the second row of outlet ports about said elongated flexible tube.

8. A method of disinfecting the interior surfaces of duct work through an access opening comprising the steps of providing an elongated flexible tube constructed of a heat sealable material having a first end, a second closed end, a visual indicator on said elongated flexible tube intermediate the first and second ends thereof, and an array of outlet ports formed partially along the length of said tube between the visual indicator and the second closed end of said tube, inserting the second end of said tube through the access opening into the duct work until the visual indicator is coplanar with the access opening to position the array of outlet ports inside the duct work, and providing disinfectant under pressure to the first end of the tube, whereby the disinfectant issues from the outlet ports as an aerosol cloud that collects on and disinfects the interior surfaces of the duct work.

9. The method of claim 8 and wherein the elongated flexible tube is heat sealed at its second end.

10. The method of claim 8 and further including the step of aligning said visual indicator with the access opening so that said array of outlet ports are optimally positioned within the duct work to facilitate thorough and efficient application of the aerosol cloud to the interior surfaces of the duct work.

\* \* \* \* \*